United States Patent [19]

Frazier

[11] Patent Number: 4,980,482

[45] Date of Patent: Dec. 25, 1990

[54] PROCESS FOR THE PREPARATION OF N-MALEOYL ACTIVATED ESTERS OF AMINO ACIDS

[75] Inventor: Kevin A. Frazier, Midland, Mich.

[73] Assignee: The Dow Chemical Company, Midland, Mich.

[21] Appl. No.: 145,025

[22] Filed: Jan. 19, 1988

[51] Int. Cl.$^5$ .......................................... C07D 207/452
[52] U.S. Cl. ..................................... 548/520; 548/548
[58] Field of Search ................................ 548/520, 548

[56] References Cited

U.S. PATENT DOCUMENTS 3,018,292  1/1962  Sauers .................................. 548/548

OTHER PUBLICATIONS

Yoshitake, "Conjugation of Glucose Oxidase...", Eur J. Biochem 101, 395–399 (1979).

Primary Examiner—Robert A. Wax
Assistant Examiner—Frederick F. Tsung

[57] ABSTRACT

A process for the preparation of activated esters of certain N-maleoyl amino acids is disclosed. In the process, maleamic acids are cyclized and esterified to the desired products by the initial reaction with an acid halide reagent followed by a subsequent reaction with the appropriate hydroxyl-containing compound. The activated esters of N-maleoyl amino acids are particularly suited for linking compounds containing an amino group with those containing a thiol group.

6 Claims, No Drawings

PROCESS FOR THE PREPARATION OF N-MALEOYL ACTIVATED ESTERS OF AMINO ACIDS

FIELD OF THE INVENTION

This invention relates to a process for the preparation of activated esters of certain N-maleoyl amino acids from the corresponding maleamic acids.

BACKGROUND OF THE INVENTION

N-Maleoyl amino acids and N-maleoyl peptides, as N-alkylmaleimides, are able to react rapidly and specifically with thiol groups. Carboxyl activated esters of N-maleoyl amino acids, such as, for example, the N-hydroxysuocinimide esters, are able to react rapidly with amino groups. The activated esters of N-(maleoyl amino acids, therefore, are particularly useful for linking compounds containing amino groups on the one hand to compounds containing thiol groups on the other hand. The utility of such compounds in preparing peptide-protein conjugates and a wide variety of other conjugates of biochemical interest in this manner have been disclosed in the following references: Keller et al., Helv. Chim. Aota, 58, 531 (1975); Wuensch et al., Biol. Chem. Hoppe-Seyler, 366, 53 (1985): Moroder et al., Biopolymers, 22, 481 (1983); Yoshitake et al., Eur. J. Biochem., 101, 395 (1979); Fujiwara et al., Cancer Research, 41, 4121 (1981); and Rich et al., J. Med. Chem., 18, 1004 (1975).

These same references also discuss the preparation of N-maleoyl amino acids and their esters. Keller et al., in one of the earliest of the above publications, reported that although maleamio acids are readily accessible by the reaction of amino acids with maleic anhydride, their subsequent cyclization to the maleimide is difficult in the presence of an additional free carboxyl group. Although maleamic acid esters had been successfully cyclized to the maleimides, Rich et al., in another of the earliest of the above publications, noted that the preferential hydrolysis of the maleimide effectively prevented the preparation of N-maleoyl amino acids from their esters. More recent approaches have appeared in the literature that avoid these difficulties in preparing activated esters of N-maleoyl amino acids. Most of these approaches require either multiple reaction steps and/or the use of relatively expensive dicyclohexyl carbodiimide. The present invention provides a convenient means of rapidly preparing the activated esters of certain N-maleoyl amino acids directly without the use of dicyclohexyl carbodiimide.

SUMMARY OF THE INVENTION

The present invention is directed to a process for the preparation of activated esters of N-maleoyl amino acids. The process of the invention is particularly directed to the N-hydroxysuccinimido, N-hydroxyphthalimido and nitrophenyl esters of N-maleoyl β-alanine and 3- and 4-amino-benzoic acids. In the process, the corresponding maleamic acids are cyclized and esterified. The maleamic acids are initially contacted with at least two (2) equivalents of an acid halide reagent at an elevated temperature. After the reaction is complete, the excess acid chloride reagent is removed and the remaining material is contacted with about one (1) equivalent of a hydroxyl containing compound, such as, for example, N-hydroxysuccinimide, N-hydroxyphthalimide, 2-nitrophenol, 4-nitrophenol and 2,4-dinitrophenol and about two (2) equivalents of a hydrogen halide acceptor. Conventional laboratory workup procedures provide an activated ester of a N-maleoyl amino acid of sufficient purity for use in the formation of biological conjugates.

DETAILED DESCRIPTION OF THE INVENTION

The present invention is a process for the preparation of activated esters of N-maleoyl amino acids of formula I

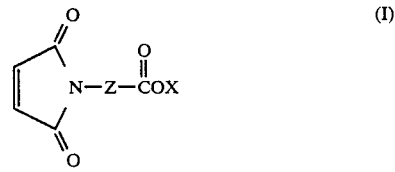

wherein Z is —CH$_2$CH$_2$—, meta- or para-phenylene; and

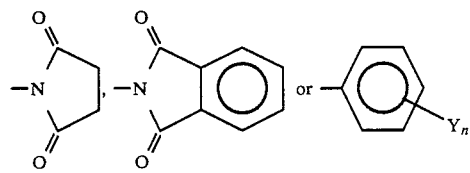

wherein Y is —NO$_2$ and n is 1 or 2
which comprises:
(a) contacting a maleamic acid of formula 11,

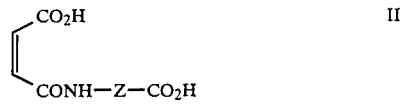

wherein Z is as previously defined, with at least two (2) equivalents of an acid halide reagent at elevated temperature;
(b) removing the excess acid halide reagent when the reaction is complete; and
(c) contacting the material remaining after the removal of the excess acid halide reagent with about one (1) equivalent of a compound of the formula HOX, wherein X is as previously defined, and about two (2) equivalents of a hydrogen halide acceptor.

The process of the present invention is particularly commendable for the preparation of activated esters of N-maleoyl β-alanine.

The starting maleamic acids are known compounds and have been described, for example, by Rich et al., J. Med. Chem., 18, 1004 (1975) and Augustin et al., J. Prakt. Chem., 327, 789 (1985). Maleamic acids can be routinely prepared by direct reaction of the amino acid with maleic anhydride.

By acid halide reagent is meant an inorganic or an organic acid halide which is commonly employed for the conversion of an organic acid into the corresponding acid halide. Such acid halide reagents can be bromides or chlorides and include, for example, thionyl chloride, phosphorus trichloride, phosphorus pentachloride, phosphorus oxychloride and oxalyl chloride.

Thionyl chloride and oxalyl chloride are the most preferred reagents because the byproducts of their reaction are gases, facilitating the simplified isolation of the product.

The reaction of the maleamic acid with the acid halide reagent can be performed in the presence of an inert solvent. Typically, however, the acid halide reagent is used as the solvent and is consequently employed in substantial excess over and above the minimum of at least two (2) equivalents of acid halide reagent that is required to insure reaction of each carboxylic acid group of the maleamic acid. The reaction is routinely conducted at elevated temperatures. Temperatures in the range of about 50° C. to about 100° C. are conveniently employed. When excess acid halide is used as the solvent, the reflux temperature is preferred. The reaction can be performed at reduced or elevated pressure, but reaction at atmospheric pressure is usually most convenient.

Excess acid halide reagent can be removed by appropriate laboratory techniques. The boiling points of the preferred acid halide reagents suggest and facilitate removal by distillation. Operation at subatmospheric pressures can aid in the removal of the last vestiges of excess reagent.

After the removal of any excess acid halide reagent, the remaining material is reacted with about one (1) equivalent of the hydroxyl compound and about two (2) equivalents of a hydrogen halide acceptor. Although of no practical advantage, larger quantities of these materials may be successfully employed.

By hydrogen halide acceptor is meant a compound that is capable of reacting with a hydrogen halide reaction byproduct in preference to any of the starting materials. Preferred hydrogen halide acceptors include pyridine and trialkylamines wherein each alkyl group, which may be the same or different, contains one (1) to four (4) carbon atoms.

The final reaction step is generally conducted in the presence of an inert organic solvent. Such solvents include, but are not limited to, conventional halogenated hydrocarbons which are particularly useful for this purpose. Temperatures in the range of about 0° C. to about 50° C. are conveniently employed.

The activated esters of the N-maleoyl amino acids can be recovered by conventional procedures, such as extraction. Generally, the products can be used without further purification. If desired, purification can be accomplished by routine procedures such as chromatography or recrystallization.

The following examples are illustrative of the invention and are not intended as a limitation thereof.

EXAMPLE 1

Preparation of Maleamic Acid of β-Alanine

β-Alanine (8.9 grams (g), 100 millimole (mmol)) was dissolved in 10 milliliter (ml) of $H_2O$. Maleic anhydride (9.8 g, 100 mmol) was added all at once and the mixture was stirred vigorously for four (4) hours at ambient temperature. After completion of the reaction, the mixture was filtered and the white powder obtained was washed with several volumes of $H_2O$ followed by anhydrous ethanol, and then anhydrous ether. After drying, 11.5 g of the maleamic acid was obtained.

EXAMPLE 2

Preparation of N-Hydroxysuccinimide Ester of N-Maleoyl β-Alanine

The maleamic acid of Example 1 (1 g, 5.35 mmol) was stirred in 20 ml of thionyl chloride and heated at reflux until gas evolution had ceased (approximately one (1) hour). The excess $SOCl_2$ was removed by distillation under reduced pressure, carbon tetrachloride was added to the remaining material, and the resulting solution was evaporated under reduced pressure to insure complete removal of $SOCl_2$. The resulting product was dissolved in 20 ml $CH_2Cl_2$ and was slowly added to a stirred mixture of N-hydroxysuccinimide (0.62 g, 5.35 mmol) and triethylamine (1.64 ml, 11.8 mmol) in 20 ml of $CH_2Cl_2$ cooled to 0° C. After the addition was complete, the reaction mixture was allowed to warm to room temperature. After stirring an additional one-half hour at room temperature, the reaction mixture was diluted with 200 ml of $CH_2Cl_2$ and was washed twice with $H_2O$ and once with brine. The solution was dried over $Na_2SO_4$ and the solvent was removed under reduced pressure. The product (1.2 g) was obtained as a light tan solid with a melting point of 156°–160° C.

EXAMPLE 3

Preparation of N-Hydroxysuccinimide Ester of N-Maleoyl 3-Aminobenzoic Acid

The process of Example 2 was repeated substituting an equivalent molar amount of the maleamic acid derived from 3-aminobenzoic acid for the maleamic acid derived from β-alanine. The desired product was isolated in a 91 percent yield.

EXAMPLE 4

Preparation of 4-Nitrophenyl Ester of N-Maleoyl β-Alanine

The process of Example 2 was repeated substituting an equivalent molar amount of para-nitrophenol for N-hydroxysuccinimide. The desired product was isolated in an 88 percent yield.

What is claimed is:

1. A process for the preparation of activated esters of N-maleoyl amino acids of formula I,

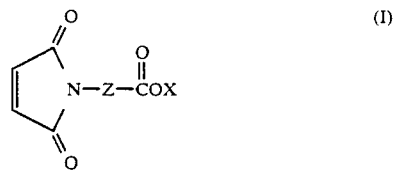

wherein

Z is —$CH_2$—, meta- or paraphenylene; and

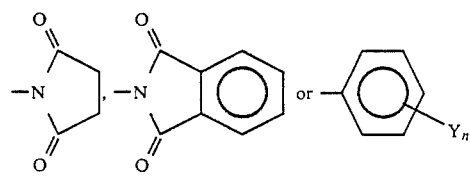

wherein

Y is —$NO_2$ and n is 1 or 2 which comprises:

(a) contacting a maleamic acid of formula II,

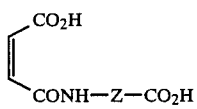
(II)

wherein

Z is as previously defined, with at least two (2) equivalents of an acid halide reagent at elevated temperature;

(b) removing the excess acid halide reagent when the reaction is complete; and (c) contacting the material remaining after the removal of the excess acid halide reagent with about one (1) equivalent of a compound of the formula HOX, wherein X is as previously defined, and about two (2) equivalents of a hydrogen halide acceptor.

2. A process according to claim 1 wherein the acid halide reagent is selected from the group consisting of thionyl chloride and oxalyl chloride.

3. A process according to claim 1 wherein the hydrogen halide acceptor is selected from the group consisting of pyridine and trialkylamines wherein each alkyl group, which may be the same or different, contains one to four carbon atoms.

4. A process according to claim 1 wherein Z is —CH$_2$CH$_2$—.

5. A process according to claim 1 wherein Z is meta- and para-phenylene.

6. A process for the preparation of

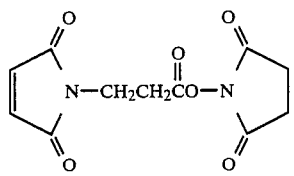

which comprises:

(a) contacting

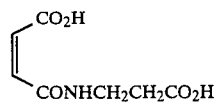

with at least two equivalents of thionyl chloride at elevated temperature;

(b) removing the excess thionyl chloride when the reaction is complete; and (c) contacting the material remaining after the removal of the excess thionyl chloride with about one equivalent of N-hydroxysuccinimide and about two equivalents of a trialkylamine wherein each alkyl group, which may be the same or different, contains one to four carbon atoms.

* * * * *